United States Patent [19]

Crudden

[11] Patent Number: 5,386,043
[45] Date of Patent: Jan. 31, 1995

[54] NON-AQUEOUS NEUTRALIZATION OF N-ACYL SARCOSINES

[75] Inventor: Joseph J. Crudden, Hudson, N.H.

[73] Assignee: Hampshire Chemical Corp., Lexington, Mass.

[21] Appl. No.: 255,183

[22] Filed: Jun. 7, 1994

[51] Int. Cl.$^6$ ............................................. C07C 231/12
[52] U.S. Cl. ........................................ 554/68; 554/63; 554/70
[58] Field of Search ................................... 554/63, 70

[56] References Cited

U.S. PATENT DOCUMENTS

| | | | |
|---|---|---|---|
| 3,450,752 | 6/1969 | Inklaar | 260/534 |
| 3,836,551 | 9/1974 | Schroeder et al. | 260/404 |
| 4,436,910 | 3/1984 | Kleemann et al. | 546/245 |
| 5,186,855 | 2/1993 | Crudden . | |

FOREIGN PATENT DOCUMENTS 1486988  6/1967  France .

Primary Examiner—José G. Dees
Assistant Examiner—Deborah D. Carr
Attorney, Agent, or Firm—Nields & Lemack

[57] ABSTRACT

A process for the non-aqueous neutralization of N-Acyl sarcosines. N-Acyl sarcosines are neutralized with anhydrous hydroxide or with hydroxide with low water content, ideally less than 20% water, using high shear. The process eliminates numerous stages previously required on route to a 100% active product. In addition, 30% solutions can be produced by the instant process, with the advantage of avoiding pH ranges at which gel phases or liquid crystals form.

5 Claims, No Drawings

NON-AQUEOUS NEUTRALIZATION OF N-ACYL SARCOSINES

BACKGROUND OF THE INVENTION

The use of sarcosinate surfactants, and in particular, N-Acyl sarcosinates in the manufacture of soaps and for other personal care and industrial applications is well known. Typically, the sarcosinate is used in the form of its sodium, potassium or ammonium salt solution. N-Acyl sarcosinates are produced commercially by the Schotten-Baumann reaction of the sodium salt of sarcosine with the appropriate fatty acid chloride under carefully controlled conditions:

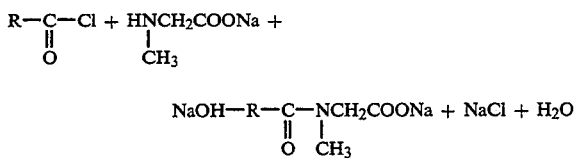

where R is typically a fatty acid of chain length $C_{10}$ to $C_{18}$, commonly made from lauric, coconut, palmitic, myristic or oleic acid. After the reaction is complete, the crude sodium salt is acidified to liberate the free fatty sarcosine acid which is separated from the aqueous by-products. It then is neutralized to a salt form. Sarcosinates such as sodium lauroyl sarcosinate, sodium cocoyl sarcosinate and sodium myristoyl sarcosinate are commercially available under the trademark HAMPOSYL® from Hampshire Chemical Corp., as 30% active solutions in water. To produce soap bars, much of the water is removed, which may require heating the mixture to temperatures in the vicinity of 150° C. The 30% solutions are costly to package and ship, and require preservatives, which are coming under close scrutiny. Some are toxic, potential carcinogens or sensitizers. Formaldehyde, which was previously used to preserve sarcosinates, is no longer acceptable. It is more favorable to ship an unpreserved raw material and allow the customer to preserve his finished product as he wishes, since different customers favor different preservative systems. Unlike aqueous solutions, the solid products are not susceptible to biodegration.

More concentrated sarcosinate solutions are difficult to produce because of high viscosity. Furthermore, as the pH of the N-Acyl sarcosine is raised from pH 2 towards pH 5, even enroute to 30% solutions gel phases of high viscosity are often encountered (particularly with myristoyl and oleoyl sarcosines), which make production of a uniform and homogeneous product difficult and time consuming. Above 30% concentrations, at any pH, the solutions become too viscous to handle. This is why solutions are offered at 30% concentrations. (Sodium oleoyl sarcosinate is not offered as a solution because it becomes too viscous to hande above 15% active.) As a result, when a product of nearly 100% activity is required, the 30% solution must be spray dried, which is a difficult and costly process.

It is therefore an object of the present invention to provide a process for producing concentrated sarcosinate solutions while avoiding the viscous, gel phases typically encountered in prior art processes. Benefits of concentrated product include reduced shipping cost and no requirements for preservatives.

SUMMARY OF THE INVENTION

The problems of the prior art have been overcome by the instant invention, which provides a process for the non-aqueous neutralization of N-Acyl sarcosines. Generally, the instant process involves neutralization of N-Acyl sarcosines with anhydrous hydroxide or with hydroxide with low water content, ideally less than 20% water, using high shear. The process eliminates numerous stages previously required on route to a 100% active product. In addition, 30% solutions can be produced by the instant process, with the advantage of avoiding pH ranges at which gel phases or liquid crystals form.

DETAILED DESCRIPTION OF THE INVENTION

Suitable N-Acyl sarcosines for the present invention include myristoyl sarcosine, oleoyl sarcosine, cocoyl sarcosine, lauroyl sarcosine, stearoyl safcosine and palm kernel sarcosine.

The pure N-Acyl sarcosine can be easily neutralized using a base, preferably an alkali metal hydroxide, most preferably sodium hydroxide or potassium hydroxide pellets. Typically sodium hydroxide pellets contain about 4% water. If alkali containing higher amounts of water, such as 50% or 80% sodium hydroxide is used, it will be necessary to add it gradually with the system held at high temperature (100°–150° C.). This will prevent the water content from rising sufficiently to gel the system, since these elevated temperatures over a prolonged period with the presence of significant quantities of water will lead to hydrolysis of some of the acyl sarcosine, resulting in increased fatty acid and other residues in the system. The color of a solution of the finished product will also increase.

When subjected to high shear, clear, pure liquid sodium N-acyl sarcosine is produced which rapidly solidifies on cooling to a brittle solid. This solid is easily dissolved in water to produce a clear solution of about pH 7. No gel phases are encountered since the process avoids pH range at which such phases occur. Sodium N-acyl sarcosine also can be prepared as a 10% solution having a pH of 7.5 to 8.5, consistent with commercial specifications.

Preferably the sarcosine is heated to a temperature in the range of 60° to 80° C. or higher, and sufficient solid base is added to produce a product that when dissolved in water, has a pH of about 7 (a pH of about 7 to 8 requires approximately a 1:1 mole ratio). The mixture is then strongly agitated to cause the pellets to dissolve and react. Upon cooling, the product solidifies and can be micronized to a fine powder where desired. Sufficient water is not present to form liquid crystal or gel phases which would make mixing extremely difficult. The amount of water present is an essential characteristic of these viscous phases; the more residual water, the greater the tendency for viscosity to increase and hydrolysis of the product to occur.

In order to obtain the high shear necessary to practice the instant invention, a mixer such as the Bamix Biomixer Homogenizer having a power rating of 85 watts and motor speed of up to 10,000 rpm has been found to be suitable for laboratory purposes when used with the chopper or so-called "C" blade. Other high shear mixers suitable for plant operation include in-line high shear mixers available from Silverson Machines Limited. The caustic pellets can be fed continuously to the system via loss-in-weight feeders such as those available from AccuRate, Inc., with an accuracy of 0.4%.

The instant invention will be better understood by referring to the following specific but nonlimiting examples. It is understood that said invention is not limited by these procedures which are offered merely as illustrations; it is also understood that modifications can be made without departing from the spirit and scope of the invention.

EXAMPLE 1

Cocoyl sarcosine, 280 grams, was heated to about 70° C. in a Pyrex beaker and 40 grams of sodium hydroxide pellets were added. The mixture was strongly agitated with a Cuisinart quick prep mixer. The pellets rapidly dissolved and reacted with the evolution of heat, the mixture reaching a temperature of over 120° C. Bubbles of steam were evolved from the mixture.

The clear, hot homogenous liquid was poured around the inside of a 5 liter beaker and rapidly solidified to a white friable solid. The solid could be easily stripped from the surface of the glass and was readily micronizable to a fine powder using a Waring blender. The product passed through a 200 mesh screen. The pH of a 10% solution of the powder was 7.85.

EXAMPLE 2

Oleoyl sarcosine, 349 grams, was reacted with 40 grams of sodium hydroxide pellets as in Example 1. The liquid solidified when poured onto the surface of the chilled glass, though not as rapidly as in the previous example. The cold solid was stripped from the glass and was found to be friable. The product was micronized in the Waring blender as before and though softer than the product of Example 1, had no tendency to cake when stored in a zipper plastic bag. The pH of a 10% solution was found to be 8.75.

EXAMPLE 3

Three batches of 270 grams of lauroyl sarcosine were reacted with a) 39.4 grams, b) 40.0 grams, and c) 40.6 grams of sodium hydroxide pellets as in the previous examples. The pH's of a 10% solution of the three products were a) 7.40, b) 7.72 and c) 8.40. The solidification temperatures of the three batches were a) 104° C., b) 120° C., and c) 114° C. respectively. About 40 grams of each batch were placed in a glass jar, covered, and placed in an oven at 130° C. overnight. The color of each sample remained very light yellow. The free fatty acid content of the three samples determined by L.C. were a) 2.0, b) 1.8 and c) 1.5. This indicates that the products are not very susceptible to thermal decomposition.

EXAMPLE 4

Stearoyl sarcosine, 338 grams, was reacted with 40 grams of sodium hydroxide as before. The product very rapidly solidified to a white friable solid when allowed to cool. The solid was easily micronized using a Waring blender and the product passed through a 200 mesh screen. The pH of a 10% solution was 7.25.

EXAMPLE 5

Myristoyl sarcosine, 120 grams, were heated to 70°-80° C. on a hot plate, in a 250 ml beaker, and 16 grams of sodium hydroxide pellets were added. The mixture was agitated with a Cuisinart Quick Prep Mixer. The pellets mixed and dissolved completely in about 1 minute with evolution of heat. No gel phase was formed and the system rapidly lost the entrained air. No pieces of residual pellets could be observed in the clear product.

The system, when heated to 100° C., began to loose the water of reaction and it should be possible to remove all of the entrained water by heating.

The clear, hot, pourable liquid was poured onto cool glass and rapidly solidified within 1 minute to an easily friable solid.

30 grams of the product was added to 70 mls of tap water and was dispersed using the Cuisinart mixer. A homogenous solution was easily formed. When some of the solution was added to tap water the pH was found to be about 7.

What is claimed is:

1. A process for the non-aqueous neutralization of N-acyl sarcosines, comprising neutralizing said N-acyl sarcosine with caustic under the application of high shear.

2. The process of claim 1 wherein said caustic is selected from the group consisting of sodium hydroxide and potassium hydroxide.

3. The process of claim 1 wherein said caustic is anhydrous sodium hydroxide.

4. The process of claim 1 wherein said caustic is sodium hydroxide having a water content of less than about 20%.

5. The process of claim 1 wherein said caustic is sodium hydroxide having a water content of about 4%.

* * * * *